(12) United States Patent  (10) Patent No.: US 8,323,318 B2
Baccelli et al.  (45) Date of Patent: *Dec. 4, 2012

(54) FLEXIBLE TIE FASTENING SYSTEM

(75) Inventors: Christian Baccelli, Saucats (FR); Regis Le Couedic, Andresy (FR); Keyvan Mazda, Paris (FR)

(73) Assignee: Zimmer Spine S.A.S., Bordeaux (FR)

( * ) Notice: Subject to any disclaimer, the term of this patent is extended or adjusted under 35 U.S.C. 154(b) by 215 days.

This patent is subject to a terminal disclaimer.

(21) Appl. No.: 12/408,592

(22) Filed: Mar. 20, 2009

(65) Prior Publication Data

US 2009/0182379 A1   Jul. 16, 2009

Related U.S. Application Data

(63) Continuation of application No. 11/996,918, filed as application No. PCT/FR2006/050909 on Sep. 20, 2006.

(30) Foreign Application Priority Data

Sep. 21, 2005   (FR) ..................................... 05 09629

(51) Int. Cl.
*A61B 17/70*   (2006.01)
(52) U.S. Cl. ........................ 606/263; 606/279
(58) Field of Classification Search .................. 606/263, 606/279, 86 A, 86 R, 74, 99, 103, 248, 249, 606/278; 623/17.11
See application file for complete search history.

(56) References Cited

U.S. PATENT DOCUMENTS

| 902,040 A | 10/1908 | Wychoff |
| 1,346,940 A | 7/1920 | Collins |
| 2,049,361 A | 7/1936 | Johan |
| 4,570,618 A | 2/1986 | Wu |
| 5,030,220 A | 7/1991 | Howland |
| 5,304,178 A | 4/1994 | Stahurski |
| 5,356,412 A | 10/1994 | Golds et al. |
| 5,413,576 A | 5/1995 | Rivard |
| 5,449,361 A | 9/1995 | Preissman |
| 5,609,634 A | 3/1997 | Voydeville |

(Continued)

FOREIGN PATENT DOCUMENTS

DE   19716504   12/1998

(Continued)

OTHER PUBLICATIONS

Machine Translation: WO2004010881. accessed on Sep. 7, 2011.*

(Continued)

*Primary Examiner* — Alvin Stewart
*Assistant Examiner* — Atiya Mahmud
(74) *Attorney, Agent, or Firm* — Seager Tufte & Wickhem LLC

(57) ABSTRACT

The present invention relates to an instrument for tensioning a flexible tie (14) used for fastening an implant on a bony element of a patient by forming a first loop around the bony element. Said instrument comprises:

a rod (42) having a first end provided with bearing means (44) for bearing against said implant;

a moving part (46) that is movable in translation and that surrounds said rod (42) over a fraction of its length, said moving part including holder means (50) for holding the end of said tie; and control means (52) mounted on said moving part (46) to cause the moving part to move relative to said rod, thereby tending to move the first end (42a) of the rod away from said moving part, thereby exerting tension on said tie relative to said implant.

23 Claims, 3 Drawing Sheets

U.S. PATENT DOCUMENTS

| | | | |
|---|---|---|---|
| 5,667,508 A | 9/1997 | Errico | |
| 5,669,917 A | 9/1997 | Sauer et al. | |
| 5,702,399 A | 12/1997 | Kilpela et al. | |
| 5,720,751 A | 2/1998 | Jackson | |
| 5,772,663 A | 6/1998 | Whiteside et al. | |
| RE36,221 E | 6/1999 | Breard | |
| 5,935,133 A | 8/1999 | Wagner et al. | |
| 5,938,663 A | 8/1999 | Petreto | |
| 5,964,769 A | 10/1999 | Wagner et al. | |
| 6,053,921 A | 4/2000 | Wagner et al. | |
| 6,086,590 A * | 7/2000 | Margulies et al. | 606/263 |
| 6,099,527 A | 8/2000 | Hochschuler et al. | |
| 6,146,386 A | 11/2000 | Blackman et al. | |
| 6,179,838 B1 | 1/2001 | Fiz | |
| 6,228,096 B1 | 5/2001 | Marchand | |
| 6,241,740 B1 | 6/2001 | Davis et al. | |
| 6,277,120 B1 | 8/2001 | Lawson | |
| 6,299,613 B1 | 10/2001 | Ogilvie et al. | |
| 6,309,390 B1 | 10/2001 | Le Couedic et al. | |
| 6,391,030 B1 | 5/2002 | Wagner et al. | |
| 6,447,518 B1 | 9/2002 | Krause et al. | |
| 6,478,798 B1 | 11/2002 | Howland | |
| 6,514,255 B1 | 2/2003 | Ferree | |
| 6,547,770 B2 | 4/2003 | Carlsson et al. | |
| 6,547,790 B2 | 4/2003 | Harkey, III et al. | |
| 6,569,164 B1 | 5/2003 | Assaker et al. | |
| 6,569,171 B2 | 5/2003 | DeGuillebon et al. | |
| 6,605,091 B1 | 8/2003 | Iwanski | |
| 6,616,669 B2 | 9/2003 | Ogilvie et al. | |
| 6,656,179 B1 | 12/2003 | Schaefer et al. | |
| 6,656,185 B2 | 12/2003 | Gleason et al. | |
| 6,682,533 B1 | 1/2004 | Dinsdale et al. | |
| 6,689,140 B2 | 2/2004 | Cohen | |
| 6,695,852 B2 | 2/2004 | Gleason | |
| 6,746,452 B2 | 6/2004 | Tuke et al. | |
| 6,773,438 B1 | 8/2004 | Knodel et al. | |
| 6,946,000 B2 * | 9/2005 | Senegas et al. | 623/17.11 |
| 7,481,828 B2 * | 1/2009 | Mazda et al. | 606/263 |
| 7,699,874 B2 | 4/2010 | Young | |
| 7,909,853 B2 * | 3/2011 | Zucherman et al. | 606/249 |
| 7,959,654 B2 | 6/2011 | Mazda et al. | |
| 2001/0034522 A1 * | 10/2001 | Frigg | 606/61 |
| 2002/0116013 A1 | 8/2002 | Gleason et al. | |
| 2002/0198538 A1 | 12/2002 | Kortenbach et al. | |
| 2003/0195628 A1 | 10/2003 | Bao et al. | |
| 2004/0087979 A1 | 5/2004 | Field et al. | |
| 2004/0138666 A1 | 7/2004 | Molz et al. | |
| 2005/0070958 A1 | 3/2005 | Swayze et al. | |
| 2005/0085815 A1 | 4/2005 | Harms | |
| 2005/0131404 A1 * | 6/2005 | Mazda et al. | 606/61 |
| 2005/0154403 A1 | 7/2005 | Sauer et al. | |
| 2005/0177156 A1 | 8/2005 | Timm et al. | |
| 2005/0228375 A1 * | 10/2005 | Mazda et al. | 606/61 |
| 2005/0267420 A1 * | 12/2005 | Young | 604/263 |
| 2006/0084988 A1 * | 4/2006 | Kim | 606/61 |
| 2006/0235387 A1 | 10/2006 | Peterman | |
| 2006/0235391 A1 | 10/2006 | Sutterlin, III | |
| 2007/0016190 A1 | 1/2007 | Martinez et al. | |
| 2007/0088359 A1 | 4/2007 | Woods et al. | |
| 2007/0299445 A1 | 12/2007 | Shadduck et al. | |
| 2008/0033557 A1 * | 2/2008 | Pasquet et al. | 623/17.16 |
| 2008/0058812 A1 | 3/2008 | Zehnder | |
| 2008/0125780 A1 | 5/2008 | Ferree | |
| 2008/0208256 A1 | 8/2008 | Thramann | |
| 2009/0131985 A1 * | 5/2009 | Mazda et al. | 606/246 |
| 2009/0138048 A1 | 5/2009 | Baccelli et al. | |
| 2009/0326585 A1 | 12/2009 | Baccelli et al. | |
| 2011/0034956 A1 | 2/2011 | Mazda et al. | |
| 2012/0022591 A1 | 1/2012 | Baccelli et al. | |

FOREIGN PATENT DOCUMENTS

| | | |
|---|---|---|
| EP | 0780096 | 6/1997 |
| EP | 1815812 | 8/2007 |
| FR | 522040 | 7/1921 |
| FR | 26156 | 9/1923 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| GB | 2269753 | 2/2004 |
| JP | 2001299770 | 10/2001 |
| WO | WO9416635 A1 | 8/1994 |
| WO | 0154599 | 8/2001 |
| WO | WO0207622 | 1/2002 |
| WO | 0209604 A1 | 2/2002 |
| WO | WO0209604 A1 | 2/2002 |
| WO | WO0217803 A2 | 3/2002 |
| WO | WO02051326 A1 | 7/2002 |
| WO | WO02071960 A1 | 9/2002 |
| WO | WO 03007829 A1 | 1/2003 |
| WO | WO03103519 A1 | 12/2003 |
| WO | 2004010881 | 2/2004 |
| WO | WO2004010881 A1 | 2/2004 |
| WO | WO 2004010881 A1 * | 2/2004 |
| WO | WO 2005020860 A3 | 3/2005 |
| WO | WO2005120277 A1 | 12/2005 |
| WO | WO 2006106268 A3 | 10/2006 |
| WO | WO 2006106246 | 12/2006 |
| WO | WO 2007023240 A3 | 3/2007 |
| WO | WO2007034112 A1 | 3/2007 |
| WO | WO 200736657 | 4/2007 |
| WO | WO2007099258 A2 | 9/2007 |

OTHER PUBLICATIONS

European Search Report for EP 08305124.3, dated Oct. 20, 2008, 3 pages.
English Translation of International Preliminary Report for PCT/FR2006/050898 on Patentability Chapter I, dated Apr. 29, 2008, 6 pages.
English Translation of International Preliminary Report on Patentability Chapter I for PCT/FR2006/050909, dated Apr. 8, 2008, 5 pages.
English Translation of the Written Opinion of the International Search Authority for PCT/FR2006/050909, dated Apr. 2, 2008, 4 pages.
English Translation of the Written Opinion of the International Search Authority for PCT/FR2006/050898, dated Apr. 28, 2008, 5 pages.
European Search Report for EP 08305183, dated Mar. 19, 2009, 10 pages.
European Search Report for EP 08305326, dated Nov. 12, 2008, 3 pages.
European Search Report for EP 2052689, dated Apr. 15, 2008, 6 pages.
European Search Report issued in EP 08305326 on Nov. 18, 2006, 5 pages.
French Preliminary Search Report and Written Opinion for FR200650609, dated Jun. 30, 2006, 5 pages.
International Search Report for WO2009053423, dated May 19, 2009, 4 pages.
International Search Report mailed Nov. 24, 2008 for PCT/EP2008/063682, 3 pages.
International Search Report for PCT/FR2006/050909 published as WO/2007/034112, dated Jan. 24, 2007, 3 pages.
Office Action for U.S. Appl. No. 10/521,914, dated Dec. 29, 2006, 21 pages.
Office Action for U.S. Appl. No. 10/521,914, dated Mar. 19, 2008, 7 pages.
Office Action for U.S. Appl. No. 10/521,914, dated Jun. 16, 2006, 13 pages.
Office Action for U.S. Appl. No. 10/521,914, dated Jul. 30, 2007, 13 pages.
International Search Report and Written Opinion for PCT/US2009/038977 mailed Jul. 22, 2009, 13 pages.
Korean Examination report for Korean Patent Application No. 1020057001238 mailed Feb. 23, 2010, 3 pages.

French Preliminary Search Report for FR0209317, dated Apr. 9, 2003, 1 page.
French Preliminary Search Report for FR0509629, mailed Jun. 9, 2006, 2 pages.
International Search Report for FR200302307, dated Jan. 2, 2004, 2 pages.
Australian Search Report for Australian Patent Application No. 2003267529, dated Nov. 15, 2007, 2 pages.
French Preliminary Search Report FR0509570, dated Jun. 29, 2006, 2 pages.
International Search Report for PCT/FR2006/050898, dated Feb. 2, 2007, 2 pages.
Written Opinion for PCT/US2009/038977, mailed Feb. 24, 2010, 7 pages.
European Search Report for European Patent Application No. 07 301 454.0, mailed Sep. 25, 2008, 8 pages.
Partial European Search Report issued in European Application No. 07 301 483.9, completed Apr. 15, 2008, mailed Apr. 23, 2008, 6 pages.
European Search Report and Search Opinion issued in European Application No. 07 301 483.9, completed Apr. 15, 2008, mailed Jul. 10, 2008, 10 pages.
International Search Report and Written Opinion issued in PCT Application No. PCT/EP2008/064344, completed Jan. 16, 2009, mailed May 19, 2009, 11 pages.
International Preliminary Report on Patentability issued in International Patent Application No. PCT/EP2008/063682, Apr. 13, 2010, 8 pages.
International Preliminary Report on Patentability issued in International Patent Application No. PCT/EP2008/064344, Apr. 27, 2010, 8 pages.
International Preliminary Report on Patentability issued in International Patent Application No. PCT/US2009/038977, May 27, 2010, 2 pages.
International Search Report issued in International Patent Application No. PCT/EP2008/064344, published as WO/2008/053423, mailed May 19, 2009, 5 pages.
International Search Report and Written Opinion issued in International Patent Application No. PCT/EP2008/063682, mailed Nov. 24, 2008, 11 pages.
International Search Report and Written Opinion issued in International Patent Application No. PCT/FR2006/050909, published as WO/2007/034112, mailed Jan. 24, 2007, 10 pages.
Office Action issued in U.S. Appl. No. 12/358,748, mailed Sep. 15, 2010, 7 pages.
Office Action issued in U.S. Appl. No. 11/877,160, mailed Nov. 26, 2010, 10 pages.
Office Action issued in U.S. Appl. No. 11/996,918, mailed Feb. 14, 2011, 12 pages.
Office Action issued in U.S. Appl. No. 12/059,634, mailed Feb. 15, 2011, 14 pages.
Notice of Allowance issued in U.S. Appl. No. 12/358,748, mailed Feb. 23, 2011, 5 pages.
Office Action issued in U.S. Appl. No. 11/877,160, mailed Apr. 12, 2011, 12 pages.
European Search Report issued in European Patent Application No. EP08305124.3, Oct. 24, 2008, 4 pages.
Office Action issued in U.S. Appl. No. 11/996,918, mailed Aug. 17, 2011, 11 pages.
Notice of Allowance issued in U.S. Appl. No. 12/375,265, mailed Aug. 25, 2011, 10 pages.
Office Action issued in U.S. Appl. No. 12/059,634, mailed Oct. 5, 2011, 12 pages.
Notice of Allowance issued in U.S. Appl. No. 11/877,160, mailed Oct. 31, 2011, 7 pages.
Notice of Allowance issued in U.S. Appl. No. 11/996,918, mailed Dec. 19, 2011, 9 pages.

* cited by examiner

US 8,323,318 B2

FLEXIBLE TIE FASTENING SYSTEM

CROSS-REFERENCE TO RELATED APPLICATION

This application is a continuation of, and claims a benefit of priority under 35 U.S.C. 120 of the filing date of U.S. patent application Ser. No. 11/996,918, filed Jan. 25, 2008, entitled "An Instrument for Tensioning a Flexible Tie," which is the National Stage of International Application No. PCT/FR2006/050909, filed Sep. 20, 2006, which claims priority to French Patent Application No. 0509629, filed on Sep. 21, 2005, the content of each application referenced herein is hereby incorporated as if fully set forth herein.

TECHNICAL FIELD OF THE INVENTION

The present invention relates to an instrument for tensioning a flexible tie used for fastening an implant on a bony element by forming a first loop around the bony element.

BACKGROUND OF THE RELATED ART

The spine is made up of a superposition of vertebrae, that are normally aligned along a vertebral axis, going from the lumbar vertebrae to the cervical vertebrae, with each vertebra presenting a posterior wall from which there projects a spinous process and two side edges having walls from which there project the ribs and/or transverse processes. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve.

In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices are used that have screws for insertion into the vertebrae or hooks for inserting along the inside wall of the spinal canal, associated with rods for interconnecting the screws or the hooks.

SUMMARY OF THE INVENTION

The hooks are generally inserted in pairs in each vertebra and on either side close to the pedicles, the heads of the hooks projecting from the posterior wall of a vertebra, one on either side of the spinous process. The heads may be tulip-shaped, for example, and they are suitable for receiving a rod which is secured by means of a nut screwed onto the head and bearing against the rod. Rows constituted by the heads of the hooks situated on either side of the spinous processes are interconnected and held in fixed position by two rods that are parallel to each other and to the axis of the spine.

Nevertheless, using such hooks is tricky, since under no circumstances must the operator harm the spinal cord that extends in the center of the spinal canal, since that would lead to paralysis for the patient.

The use of screws makes it possible to reduce the risks of such surgery. They likewise have tulip-shaped heads and they are inserted in pairs in the posterior walls of vertebrae in the pedicles on either side of the spinous processes. Thus, the screws constitute fastening points in the vertebrae for holding them relative to one another. Nevertheless, the screws are necessarily inserted into the pedicles of the vertebrae, and under certain circumstances, the pedicles may be small in size or they may be damaged.

A problem which arises, and which the present invention seeks to solve, is how to obtain such fastening points when it is not possible to introduce screws into the vertebrae in the curved portion, and when using hooks would be too dangerous.

In PCT patent application WO 2004/010881 in the name of the Applicant, a vertebral fastener system is described that enables this problem to be solved.

That vertebral fastener system suitable for mounting on a vertebra of the spine for connection to a rod comprises:
 a connection piece disposed facing said rib and/or said transverse process, and suitable for being connected to said rod;
 a flexible tie of elongate shape suitable for connecting together said connection piece and at least one rib and/or transverse process; and
 adjustable locking means secured to said connection piece, said tie presenting a first end secured to said connection piece and a free second end suitable for sliding in said connection piece and to form a loop, said locking means being suitable for simultaneously holding said connection piece in a fixed position relative to the rod and a portion of said tie extending between said ends being suitable for being locked in translation relative to said connection piece by said adjustable locking means, whereby the loop presents a length that is determined in such a manner as to prevent relative displacement of said rod and of said vertebra in opposite directions.

Other flexible tie systems for fastening to a vertebra can be used. This applies in particular to the system shown in accompanying FIG. 1.

It comprises a connection piece 12 constituted by two jaws 20 and 22 that are hinged together at one end about an axis 24. The two jaws have recesses enabling a rod 18 to be put into place and allowing a braid or tie 14 to pass through, the tie forming a loop 28 on one side of the connection piece 12 and two free ends 30 and 32 on the other side of said piece. The connection system also has a locking member constituted by a screw 16 that can be engaged in the ends of the jaws 20 and 22 remote from their hinged ends. The portions of the tie 14 that are engaged in the recesses are secured to the connection piece by being pinched between the walls of the recesses in the connection piece and the rod 18 when the locking screw 16 is fully tightened.

It can be understood that in order to ensure that said assembly is properly fastened on a transverse process, on a rib, or on a portion of the posterior arc of a vertebra, it is necessary to exert tension on the free ends 30 and 32 of the tie 14.

It will also be understood that with the first-described fastener system, it is also necessary to exert tension on the single free end of the tie in order to ensure correct fastening on the bony element.

U.S. Pat. No. 5,964,769 discloses a device serving to exert tension on a cable used for fastening a medical device on a bone. That device presents the drawbacks of acting directly on the tie-tightening device and no disposition allows the tension exerted on the tie to be controlled.

An object of the present invention is to provide an instrument for tensioning a flexible tie of an implant that ensures that it is tensioned effectively while nevertheless being easy for the surgeon to use.

To achieve this object, the invention provides an instrument for tensioning a flexible tie used for fastening an implant onto a bony element of a patient by forming a first loop around the bony element, said tie presenting at least one end that projects out from said implant, and said instrument being characterized in that it comprises:

a rod having a first end provided with bearing means for bearing against said implant;

a moving part that is movable in translation and that surrounds said rod over a fraction of its length;

holder means for holding the end of said tie, said holder means being connected to said moving part by a dynamometer system; and control means mounted on said moving part to cause the moving part to move relative to said rod, thereby tending to move the first end of the rod away from said moving part, thereby exerting tension on said tie relative to said implant.

It will be understood that since the rod bears against the implant, the moving part is secured either to the second loop of the tie, or to the free end of said tie serves to exert tension on said tie, thereby ensuring appropriate tightening of the first loop of the tie on the bony element.

In addition, when the surgeon acts on the control means, the surgeon knows when the appropriate tension has been applied, thus making it possible to avoid untimely breaking of the tie or damage to the bony element.

Preferably, the instrument further comprises an anti-return system for temporarily preventing said rod and said moving part moving in translation relative to each other, in the absence of action on the control means.

Preferably, the dynamometer system comprises a carriage that is movable in translation relative to the rod and to the moving part, said tie-holder stud being secured to said carriage, and a compression spring being interposed between said carriage and a portion of the moving part.

Also preferably, the control means comprise a trigger mounted to pivot relative to the moving part and presenting a manual actuator portion and a finger that acts on said rod.

Also preferably, the instrument further comprises a handle secured to said moving part and disposed in such a manner that the user can grasp said trigger and said handle simultaneously.

BRIEF DESCRIPTION OF THE DRAWINGS

Other characteristics and advantages of the invention appear better on reading the following description of an embodiment of the invention given by way of non-limiting example. The description refers to the accompanying figures, in which.

DETAILED DESCRIPTION

Figure 2:
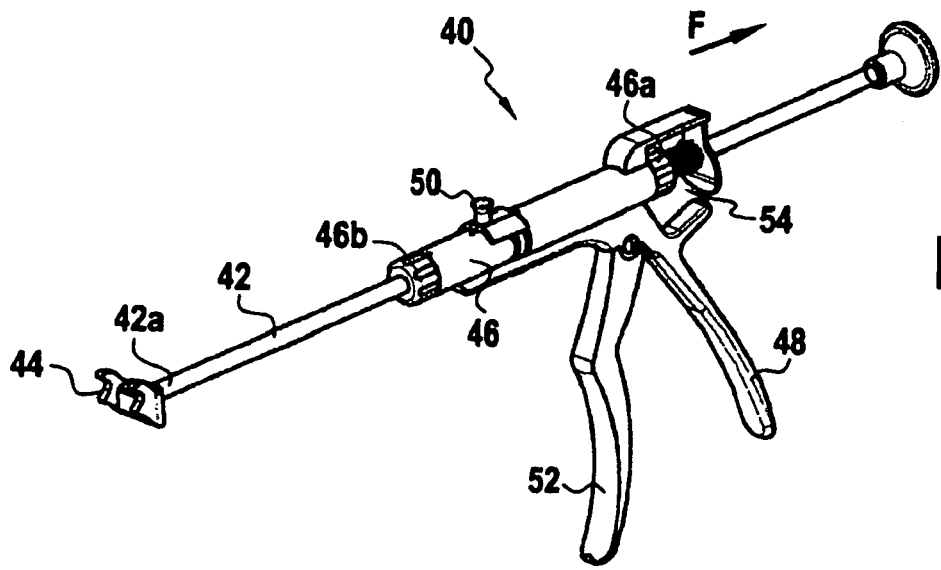
FIG. 2 is a perspective view of the instrument assembly of the invention.

With reference initially to FIG. 2, there follows a description of the instrument assembly 40. It is essentially constituted by a rod 42 having a first end 42a fitted with bearing means 44 for bearing against the implant on which the tie is to be tensioned. The instrument 40 also has a moving part 46 that is movable in translation relative to the rod 42. The moving part 46 is generally cylindrical in shape and is provided with a handle 48. The moving part 46 also has a stud 50 on its portion remote from the handle 48. As explained below, the stud 50 serves to hold the tie on which tension is to be applied. The instrument 40 also comprises a control member constituted by a trigger 52. As explained below, actuating the trigger 52 serves to cause the moving part 46 to move rearwards relative to the rod 42 in the direction of arrow F. In addition, at its end 46a opposite from its end 46b closest to the bearing element 44, the moving part 46 is fitted with an anti-return system acting on the rod 42. As explained in greater detail below, the anti-return system 54 enables the rod 42 and the moving part 46 to be held together temporarily in translation so long as no action is exerted on the trigger 52.

Figure 1:
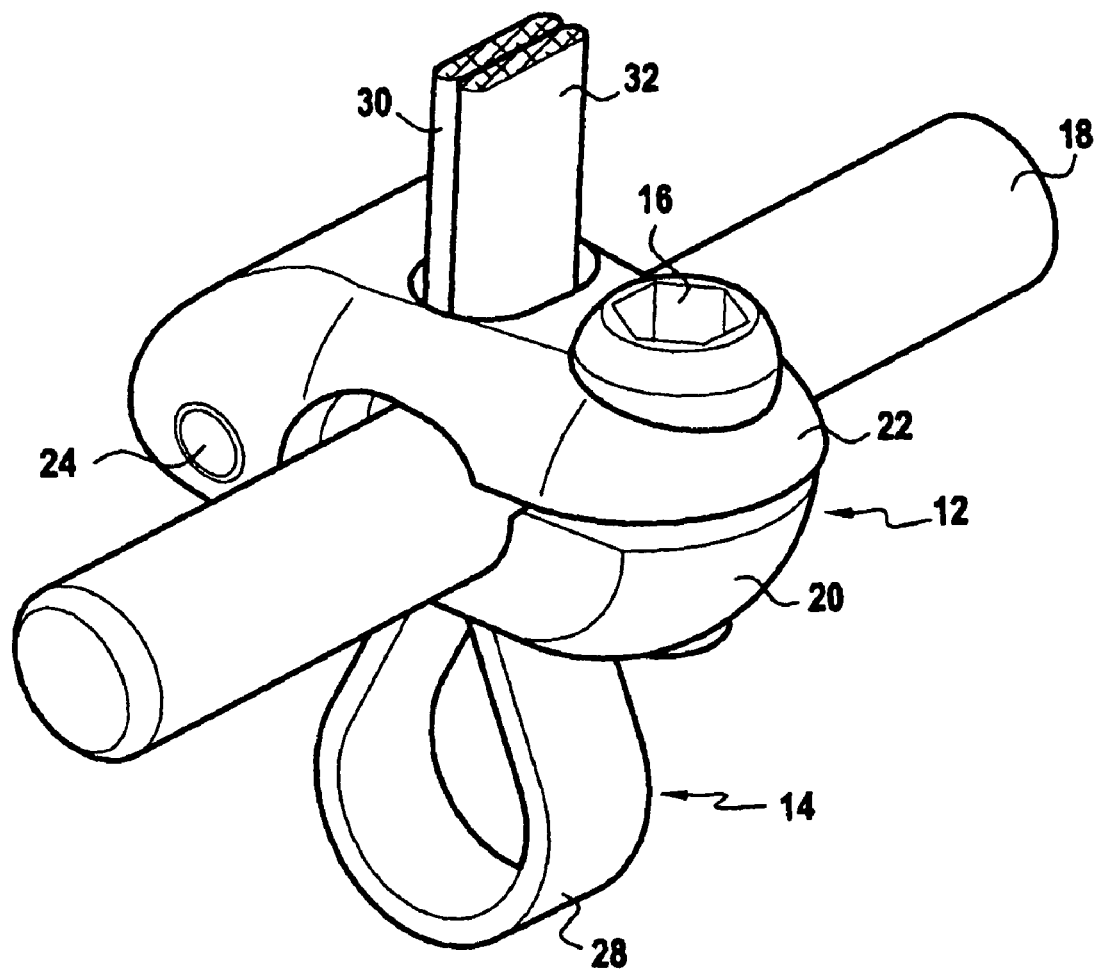
FIG. 1, described above, shows an example of an implant with a fastener tie with which the instrument of the invention can advantageously be used.
Figure 4:
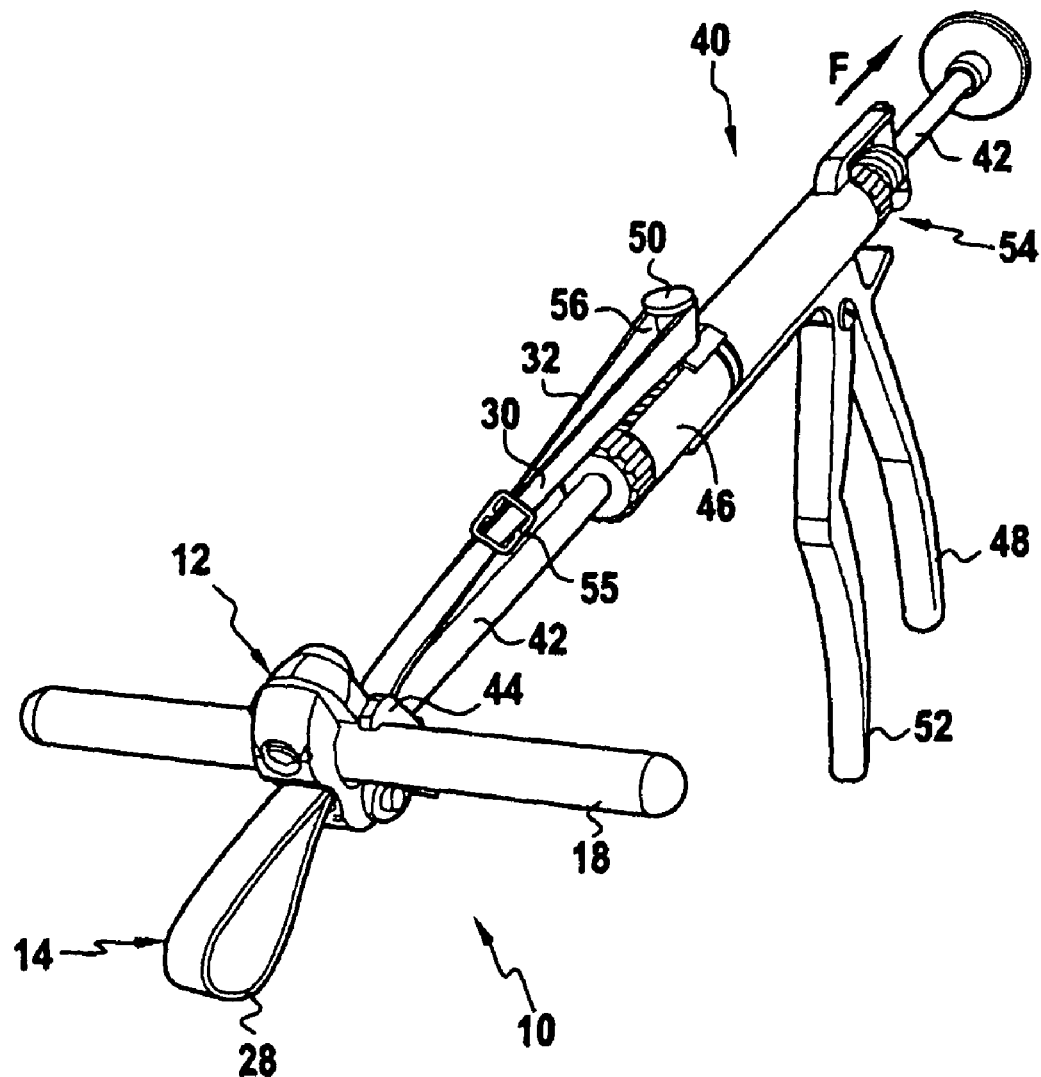
FIG. 4 is a perspective view showing the instrument in use with an implant of the type shown in FIG. 1.

With reference more particularly to FIG. 4, there follows a description in general terms of how the instrument 40 is used. In this figure, there can be seen a vertebral fastener system 10 of the type shown in FIG. 1. In this figure, there can be seen the rod 18, the connection piece 12, and the first fastener loop 28 formed by the tie 14 of the fastener system. This figure also shows that the free end 32 of the tie 14 is connected to the other free end 30 of the same tie by a fastener element 55 of suitable type. Thus, the tie 14 forms a second loop 56.

In use, the bearing means 44 of the instrument bear against the rod 18 on either side of the connection piece 12. The second loop 56 of the tie 14 is engaged on the stud 50 of the moving part 46 of the instrument. It will be understood that when the surgeon exerts action by using the trigger 52 and the handle 48, this causes the moving part 46 to move backwards in the direction F relative to the rod 18, thereby applying traction to the tie as a whole, and in particular to its loop 28. The surgeon can exert successive actions on the trigger 52 because of the presence of the anti-return system 54. As explained below, the instrument is preferably also fitted with a dynamometer system that enables the surgeon to see when a suitable tension has been exerted on the tie 14. Once the suitable tension has been exerted, the instrument 40 is separated from the loop 56 in the tie 14, and the portions of the tie 14 that project beyond the connection piece 12 are cut off.

Figure 3:
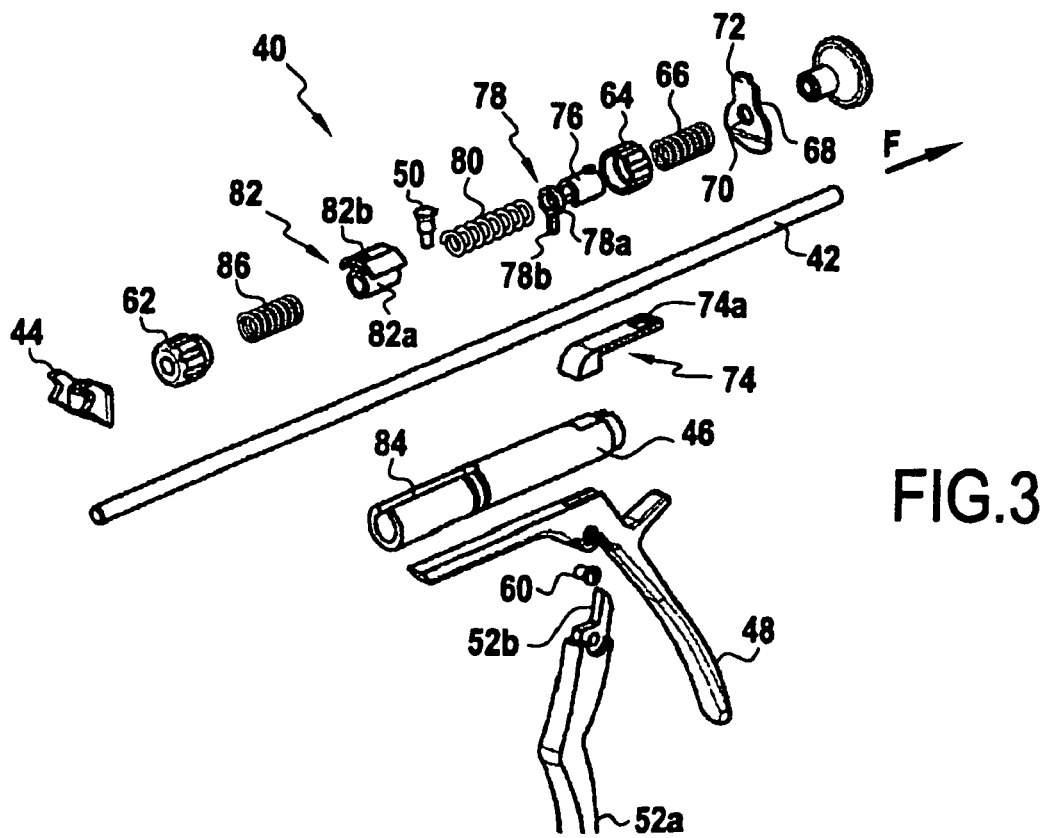
FIG. 3 is an exploded view of the disassembled instrument showing its internal mechanisms.

With reference to FIG. 3, there follows a description in greater detail of the mechanisms of the instrument 40. This figure shows the cylindrically-shaped moving part 46 on which the handle 48 is secured. The trigger 52 is hinged relative to the handle 48 about a pin 60. The trigger 52 has a grip portion 52a and a finger 52b for controlling the rod 42, for which finger 52b projects beyond the pivot pin 60. The finger 52b penetrates into the moving part 46 via a slot (not shown). The rod 42 is slidably engaged in the moving part 46.

Various elements that are described below are mounted around the rod 42 inside the moving part 46 having open ends that are closed by endpieces 62 and 64 each pierced by an axial bore for passing the rod 42. A spring 66 and a plate 68 constituting the anti-return system are mounted outside the moving part 46, around the rod 42. The plate 68 is pierced by a bore 70 of diameter that is slightly greater than the diameter of the rod. The plate 68 has a tongue 72 that can bear against an arm 74 secured to the rear portion of the moving part 46. Inside the moving part 46 and starting from its end closed by the endpiece 64, there is a spacer cylinder 76, a transmission part 78 constituted by an annular portion 78a and by a stud 78b suitable for co-operating with the finger 52b of the trigger 52. The transmission part 78 is associated with a spring 80. Thereafter there is a carriage 82 having a cylindrical portion 82a engaged around the rod 42 and two external projections 82b. The projections 82b of the carriage 82 are external to the moving part 46 by virtue of a longitudinal slot 84 therein. This external portion of the carriage 82 has the tie-holding stud 50 secured thereto. The carriage 82 is associated with a dynamometer spring 86 which is interposed between the endpiece 62 and the front face of the cylindrical portion 82*a* of the carriage 82.

In the absence of any action on the trigger 52, the plate 68 of the anti-return system slopes relative to the rod 42 because of the presence of the end 74*a* of the arm 74, thus causing the rod 42 and the moving part 46 to be temporarily secured to each other in translation. When action is exerted on the trigger 52, the movement of the rod releases the plate 68 and thus allows the rod 42 to move relative to the moving part 46. Similarly, when no action is applied to the trigger 52, the transmission part 78 is free, whereas, in contrast, when action is applied to the trigger 52, the finger 52*b* acts on the stud 78*b* of the transmission part 78, thereby temporarily securing it to the rod 42. This temporary connection serves to move the rod 42 relative to the part 46 under the effect of the trigger being actuated.

The dynamometer system operates in simple manner. Under the effect of the rod 42 moving in the direction F relative to the part 46, the dynamometer spring 86 is compressed, causing the carriage 82 to perform relative movement. A mark on the outside face of the moving part 46 makes it possible to detect when the appropriate tension has been applied, this tension corresponding naturally to the dynamometer spring 86 being subjected to predetermined compression.

In the description above, it is assumed that the tie 14 has a second loop used for holding onto the tensioning stud 50 of the instrument. When the tie of the implant has only one free end, this end can be held on the stud 50 or on any other appropriate fastener system 80 as to exert in the same manner the desired tension on the end of the tie and thus on the loop 28 formed thereby.

The invention claimed is:

1. A fastening system, comprising:
   a connection piece including a passage for receiving an elongate rod therethrough, and first and second openings on opposite sides of the connection piece;
   a tie comprising:
      two ends and an intermediate portion between the two ends, wherein the two ends of the tie are sized to pass through the first and second openings in the connection piece to form two loops:
         a first loop for engaging a bone on a first side of the connection piece, the first loop formed from the intermediate portion of the tie extending from the first opening on the first side of the connection piece; and
         a second loop for engaging an instrument on a second side of the connection piece, the second loop formed from joining the two ends of the tie extending from the second opening on the second side of the connection piece; and
      a contact portion configured to engage a surface of the connection piece; and
   an adjustable locking member configured for at least one of: holding the connection piece in a fixed position relative to a rod positioned within the passage or urging the contact portion of the tie against the connection piece to lock the tie in position,
   wherein the connection piece further comprises two jaws and a hinge joining the two jaws at an axis at a first end of the two jaws and wherein the locking member is located distal the hinge.

2. The fastening system of claim 1, wherein the locking member comprises a screw, wherein the screw engages both jaws to rotate the jaws about the axis.

3. The fastening system of claim 1, further comprising a rod contact portion of the tie, the rod contact portion of the tie pinched against a surface on the rod when the tie is locked in position.

4. A bone fastening system, comprising:
   a rod;
   a connection piece including a passage for receiving the rod therethrough, and first and second openings on opposite sides of the connection piece;
   a tie comprising:
      two ends and an intermediate portion between the two ends, wherein the two ends of the tie are sized to pass through the first and second openings in the connection piece to form a first loop from the intermediate portion of the tie extending from the first opening on a first side of the connection piece and wherein the two ends of the tie extend from the second opening on a second side of the connection piece and connect to form a second loop on the second side of the connection piece; and
      a contact portion configured to engage a surface of the connection piece; and
   a locking member configured for at least one of: holding the connection piece in a fixed position relative to the rod positioned within the passage or urging the contact portion of the tie against the connection piece to secure the tie.

5. The bone fastening system of claim 4, wherein the length of the first loop is fixed when the locking member engages the connection piece.

6. The bone fastening system of claim 4, wherein the connection piece further comprises two jaws and a hinge joining the two jaws at an axis at a first end of the two jaws, wherein the locking member is located distal the hinge.

7. The bone fastening system of claim 6, wherein the locking member comprises a screw, wherein the screw engages both jaws to rotate the jaws about the axis.

8. A method of coupling a rod to a bony element, comprising:
   positioning a rod through a passage of a connection piece;
   passing one of two ends of a flexible tie around a bony element and through at least one opening in the connection piece, wherein an intermediate portion between the two ends of the flexible tie forms a first loop around the bony element on a first side of the connection piece and the two ends extend through the connection piece and out an opening on a second side of the connection piece to form a second loop on the second side of the connection piece;
   securing the connection piece in a fixed position relative to the rod; and
   securing the flexible tie against the connection piece to fix the flexible tie relative to the connection piece,
   wherein the connection piece includes two jaws that are hingedly connected at an axis at a first end of the two jaws and wherein the locking member is located distal the hinged connection.

9. The method of claim 8, further comprising tensioning the first loop of the flexible tie around the bony element prior to securing the flexible tie against the connection piece such that the tension in the first loop is retained after securing the flexible tie against the connection piece.

10. The method of claim 9, wherein tensioning the flexible tie comprises pushing against the rod with a tensioning device while exerting tension on the two ends forming the second loop.

11. The method of claim 8, wherein the bony element comprises a vertebra or a transverse process.

12. A method for stabilizing a portion of the spine, comprising:
- positioning a rod along a portion of the spine;
- placing a first connection piece on the rod, wherein the first connection piece comprises a passage for receiving the rod and an opening;
- passing a first end of a first tie through the opening in the first connection piece;
- passing the first end of the first tie around a first vertebra, wherein an intermediate portion of the first tie between the first end and a second end of the first tie forms a first loop around the first vertebra on a first side of the first connection piece and the first and second ends form a second loop on a second side of the first connection piece;
- placing a second connection piece on the rod, wherein the second connection piece comprises a passage for receiving the rod and an opening;
- passing a first end of a second tie through the opening in the second connection piece;
- passing the first end of the second tie around a second vertebra, wherein an intermediate portion of the second tie between the first end and a second end of the second tie forms a first loop around the second vertebra on a first side of the second connection piece and the first and second ends form a second loop on a second side of the second connection piece;
- engaging a first locking member in the first connection piece to secure the first tie to the first connection piece by pressing the first tie against a surface of the first connection piece; and
- engaging a second locking member in the second connection piece to secure the second tie to the first connection piece by pressing the second tie against a surface of the second connection piece.

13. The method of claim 12, further comprising engaging the second loop in the first tie or the second tie with a tensioning tool.

14. The method of claim 12, further comprising the steps of:
- tensioning the first loop of the first tie around the first vertebra prior to engaging the first adjustable locking member such that the tension in the first loop is retained after pressing the first tie against the surface of the first connection piece; and
- tensioning the first loop of the second tie around the second vertebra prior to engaging the second adjustable locking member such that the tension in the first loop is retained after pressing the second tie against the surface of the second connection piece.

15. The method of claim 12, wherein each of the first and second connection pieces includes two jaws, wherein the two jaws of each of the first and second connection piece are hingedly connected at an axis at a first end of the two jaws, wherein the adjustable locking member is located distal the hinged connection.

16. The method of claim 15, wherein rotating the two jaws about the axis in the first connection piece pinches the first tie against the first connection piece to secure the first tie and rotating the two jaws in the second connection piece pinches the second tie against the second connection piece to secure the second tie.

17. A method for correcting a portion of the spine, comprising:
- coupling a rod to a first side of the spine, comprising:
  - positioning a rod along a portion of the spine;
  - passing a first end of a first flexible tie around a first vertebra;
  - passing a first end of a second flexible tie around a second vertebra;
  - placing the rod through a passage of a first connection piece;
  - placing the rod through a passage of a second connection piece;
  - passing the first end and a second end of the first flexible tie through an opening in the first connection piece, wherein an intermediate portion of the first flexible tie between the first end and a second end of the first tie forms a first loop on a first side of the first connection piece and the first and second ends of the first tie form a second loop on a second side of the first connection piece;
  - passing the first end and a second end of the second flexible tie through an opening in the second connection piece, wherein an intermediate portion of the second flexible tie between the first end and a second end of the second tie forms a first loop on a first side of the second connection piece and the first and second ends of the second tie form a second loop on a second side of the second connection piece;
  - tensioning the first loop of the first flexible tie with a tensioning device engaged with the first and second ends of the first flexible tie forming the second loop;
  - securing the first connection piece in a fixed position relative to the rod;
  - securing the first flexible tie against the first connection piece to fix the first loop of the first flexible tie in a tensioned state around the first vertebra;
  - positioning the second connection piece on the rod relative to the first connection piece to space the vertebrae relative to each other;
  - tensioning the first loop of the second flexible tie with a tensioning device engaged with the first and second ends of the second flexible tie forming the second loop;
  - securing the second connection piece in a fixed position relative to the rod; and
  - securing the second flexible tie against the second connection piece to fix the first loop of the second flexible tie in a tensioned state around the second vertebra
  - wherein each of the first and second connection pieces includes two jaws, wherein the two jaws of each of the first and second connection piece are hingedly connected at an axis at a first end of the two jaws, wherein the adjustable locking member is located distal the hinged connection, and further wherein rotating the two jaws about the axis in the first connection piece pinches the first flexible tie against the rod and rotating the two jaws in the second connection piece pinches the second flexible tie against the rod.

18. The method of claim 17, wherein tensioning the first flexible tie comprises pushing against the rod with the tensioning device while exerting tension on both of the first and second ends forming the second loop.

19. The method of claim 17, wherein each of the first and second flexible ties comprises a polyester material.

20. The method of claim 17, wherein the first or second flexible tie is passed around a transverse process or a rib.

21. A system for stabilizing a portion of the spine, comprising:
- a first rod for positioning on a first side of the spine relative to two or more vertebrae;
- a first connection piece, comprising:
  - a passage for receiving the first rod therethrough;
  - first and second openings on opposite sides of the connection piece; and
  - an adjustable locking member;
- a first tie comprising two ends and an intermediate portion between the two ends, wherein at least one of the two ends is passed through the first and second openings of the first connection piece to form a first loop formed by the intermediate portion of the first tie extending from the first opening on a first side of the first connection piece and wherein both ends extend from the second opening on a second side of the first connection piece to form a second loop on the second side of the first connection piece;
- a second connection piece, comprising:
  - a passage for receiving the first rod therethrough;
  - first and second openings on opposite sides of the connection piece; and
  - an adjustable locking member; and
- a second tie comprising two ends and an intermediate portion between the two ends, wherein at least one of the two ends is passed through the first and second openings of the second connection piece to form a first loop formed by the intermediate portion of the second tie extending from the first opening on a first side of the second connection piece and wherein both ends extend from the second opening on a second side of the second connection piece to form a second loop on the second side of the second connection piece;
- wherein at least one of the two ends of the first tie is tensioned to determine the length of the first loop, wherein the locking member of the first connection piece is adjustable to lock the length of the first tie in position relative to the first connection piece; and
- wherein at least one of the two ends of the second tie is tensioned to determine the length of the first loop or the second loop, wherein the locking member of the second connection piece is adjustable to lock the length of the second tie in position relative to the second connection piece.

22. The system of claim 21, wherein the length of the rod spans between two or more vertebrae and wherein the first tie or the second tie comprises polyester.

23. The system of claim 21, wherein the adjustable locking member of each of the first and second connection pieces comprises a screw, wherein the screw engages the respective connection piece to clamp the connection piece in a fixed position relative to the first rod.

* * * * *